United States Patent
Sumita

(10) Patent No.: US 9,896,354 B2
(45) Date of Patent: Feb. 20, 2018

(54) METHOD FOR PRODUCING OXIDIZED WATER FOR STERILIZATION USE WITHOUT ADDING ELECTROLYTE

(71) Applicant: TECH CORPORATION CO., LTD., Hiroshima (JP)

(72) Inventor: Osao Sumita, Tokyo (JP)

(73) Assignee: TECH CORPORATION CO., LTD., Hiroshima (JP)

( * ) Notice: Subject to any disclaimer, the term of this patent is extended or adjusted under 35 U.S.C. 154(b) by 13 days.

(21) Appl. No.: 15/037,382

(22) PCT Filed: Dec. 8, 2014

(86) PCT No.: PCT/JP2014/006119
§ 371 (c)(1),
(2) Date: May 18, 2016

(87) PCT Pub. No.: WO2015/087536
PCT Pub. Date: Jun. 18, 2015

(65) Prior Publication Data
US 2016/0272514 A1    Sep. 22, 2016

(30) Foreign Application Priority Data
Dec. 9, 2013    (JP) ................. 2013-253922

(51) Int. Cl.
*C02F 1/46*    (2006.01)
*C02F 1/461*    (2006.01)
*C02F 1/42*    (2006.01)

(52) U.S. Cl.
CPC ............. *C02F 1/4618* (2013.01); *C02F 1/42* (2013.01); *C02F 1/46109* (2013.01);
(Continued)

(58) Field of Classification Search
CPC ...... C02F 1/4618; C02F 1/46109; C02F 1/42; C02F 2303/04; C02F 2209/29;
(Continued)

(56) References Cited

U.S. PATENT DOCUMENTS

2006/0169575 A1    8/2006  Sumita
2007/0251831 A1*  11/2007  Kaczur .................. C25B 1/46
                                                        205/510
2010/0003342 A1    1/2010  Ito

FOREIGN PATENT DOCUMENTS

EP    1 103 264    5/2001
JP    11-151493    6/1999
(Continued)

OTHER PUBLICATIONS

International Search Report dated Jan. 13, 2015 in corresponding (PCT) Application No. PCT/JP2014/006119.
(Continued)

*Primary Examiner* — Arun S Phasge
(74) *Attorney, Agent, or Firm* — Wenderoth, Lind & Ponack, L.L.P.

(57) ABSTRACT

A method for producing oxidized water for sterilization use which contains chlorine dioxide, said method comprising: electrolyzing tap water containing chlorine ions using a three-chamber-type electrolysis vessel, in which an intermediate chamber is located between an anode chamber and a cathode chamber; trapping the chlorine ions dissolved in the tap water; and electrolytically oxidizing the trapped chlorine ions on an anode electrode. A partitioning membrane that isolates the anode chamber from the intermediate chamber is composed of a fluorine-containing cation exchange membrane and an anion exchange membrane, wherein a porous anode electrode is adhered onto the fluorine-containing cation exchange membrane in the partitioning membrane. A partitioning membrane that isolates the cathode chamber
(Continued)

1  POROUS ANODE ELECTRODE
2  ANODE CHAMBER
21  ANODE CHAMBER OUTLET
22  ANODE CHAMBER INLET
31  PARTITIONING MEMBRANE 1
32  PARTITIONING MEMBRANE 2
33  FLUORINE-CONTAINING CATION EXCHANGE MEMBRANE
36  NON-WOVEN FABRIC
4  CATHODE CHAMBER
41  CATHODE CHAMBER OUTLET
42  CATHODE CHAMBER INLET
5  POROUS CATHODE ELECTRODE
6  INTERMEDIATE CHAMBER
61  INTERMEDIATE CHAMBER INLET
62  INTERMEDIATE CHAMBER OUTLET
9  ANION EXCHANGE RESIN from the intermediate chamber is composed of a cation exchange membrane or an anion exchange membrane, wherein a porous cathode electrode is adhered onto the partitioning membrane; and an anion exchange resin is filled in the intermediate chamber.

8 Claims, 8 Drawing Sheets

(52) U.S. Cl.
CPC .. *C02F 2001/422* (2013.01); *C02F 2001/425* (2013.01); *C02F 2001/46161* (2013.01); *C02F 2001/46185* (2013.01); *C02F 2201/46115* (2013.01); *C02F 2209/29* (2013.01); *C02F 2209/40* (2013.01); *C02F 2303/04* (2013.01)

(58) Field of Classification Search
CPC ........ C02F 2209/40; C02F 2001/46185; C02F 2001/46161; C02F 2001/425; C02F 2001/422; C02F 2201/46115
See application file for complete search history.

(56) References Cited

FOREIGN PATENT DOCUMENTS

| | | |
|---|---|---|
| JP | 2005-58848 | 3/2005 |
| JP | 2007-268346 | 10/2007 |
| JP | 2008-119578 | 5/2008 |
| WO | 2008/072388 | 6/2008 |

OTHER PUBLICATIONS

Masahiko Takayama et al., "Bactericidal Activities of Chlorine Dioxide", J:Antibact, Antifung, •Agents, vol. 23, No. 7, 1995, pp. 401-406, with English abstract.

Mehmet Sankir, "Proton Exchange Membrane Fuel Cell Systems Based on Aromatic Hydrocarbon and Partially Fluorinated Disulfonated Poly(Arylene Ether) Copolymers", Dissertation Submitted to the Faculty of the Virginia Polytechnic Institute and State University, Dec. 6, 2005, 307 pages.

International Preliminary Report on Patentability dated Jun. 23, 2016 in International Application No. PCT/JP2014/006119P (English translation).

Extended European Search Report dated Jul. 21, 2017 in corresponding European Application No. 14869652.9.

* cited by examiner

FIG.1 - PRIOR ART

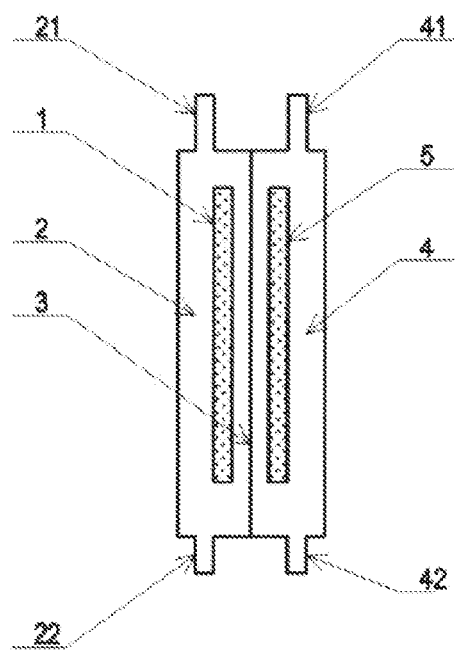

1  POROUS ANODE ELECTRODE
2  ANODE CHAMBER
21 ANODE CHAMBER OUTLET
22 ANODE CHAMBER INLET
3  PARTITIONING MEMBRANE
4  CATHODE CHAMBER
41 CATHODE CHAMBER OUTLET
42 CATHODE CHAMBER INLET
5  POROUS CATHODE ELECTRODE

FIG.2 - PRIOR ART

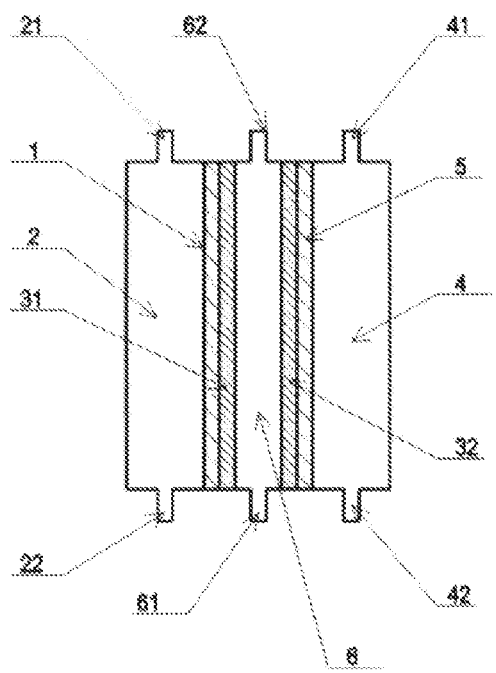

1  POROUS ANODE ELECTRODE
2  ANODE CHAMBER
21 ANODE CHAMBER OUTLET
22 ANODE CHAMBER INLET
31 PARTITIONING MEMBRANE 1
32 PARTITIONING MEMBRANE 2
4  CATHODE CHAMBER
41 CATHODE CHAMBER OUTLET
42 CATHODE CHAMBER INLET
5  POROUS CATHODE ELECTRODE
6  INTERMEDIATE CHAMBER
61 INTERMEDIATE CHAMBER INLET
62 INTERMEDIATE CHAMBER OUTLET

1   POROUS ANODE ELECTRODE
2   ANODE CHAMBER
21  ANODE CHAMBER OUTLET
22  ANODE CHAMBER INLET
31  PARTITIONING MEMBRANE 1
32  PARTITIONING MEMBRANE 2
4   CATHODE CHAMBER
41  CATHODE CHAMBER OUTLET
42  CATHODE CHAMBER INLET
5   POROUS CATHODE ELECTRODE
6   INTERMEDIATE CHAMBER
61  INTERMEDIATE CHAMBER INLET
62  INTERMEDIATE CHAMBER OUTLET
9   ANION EXCHANGE RESIN

FIG.5(a)

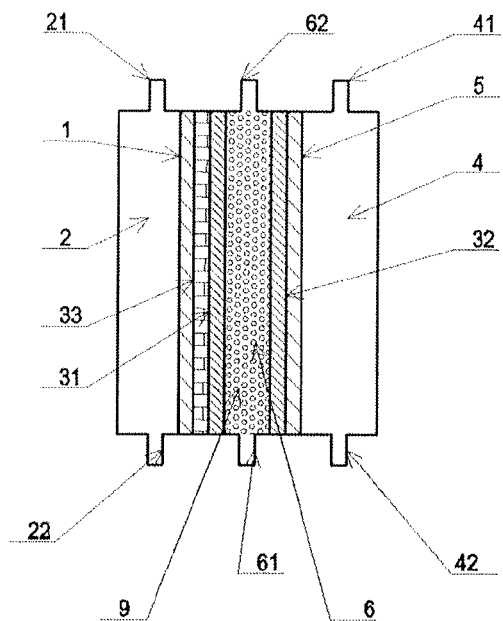

1   POROUS ANODE ELECTRODE
2   ANODE CHAMBER
21  ANODE CHAMBER OUTLET
22  ANODE CHAMBER INLET
31  PARTITIONING MEMBRANE 1
32  PARTITIONING MEMBRANE 2
33  FLUORINE-CONTAINING CATION
    EXCHANGE MEMBRANE
4   CATHODE CHAMBER
41  CATHODE CHAMBER OUTLET
42  CATHODE CHAMBER INLET
5   POROUS CATHODE ELECTRODE
6   INTERMEDIATE CHAMBER
61  INTERMEDIATE CHAMBER INLET
62  INTERMEDIATE CHAMBER OUTLET
9   ANION EXCHANGE RESIN

FIG.5(b)

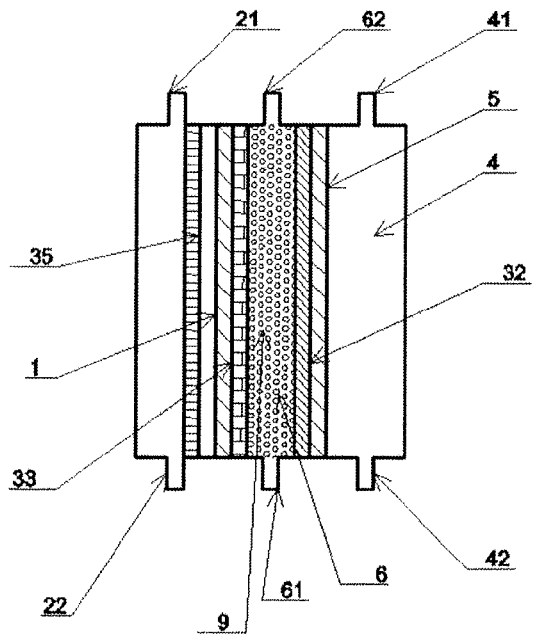

1   POROUS ANODE ELECTRODE
2   ANODE CHAMBER
21  ANODE CHAMBER OUTLET
22  ANODE CHAMBER INLET
31  PARTITIONING MEMBRANE 1
32  PARTITIONING MEMBRANE 2
33  FLUORINE-CONTAINING CATION
    EXCHANGE MEMBRANE
35  POROUS PARTITIONING PLATE
4   CATHODE CHAMBER
41  CATHODE CHAMBER OUTLET
42  CATHODE CHAMBER INLET
5   POROUS CATHODE ELECTRODE
6   INTERMEDIATE CHAMBER
61  INTERMEDIATE CHAMBER INLET
62  INTERMEDIATE CHAMBER OUTLET
9   ANION EXCHANGE RESIN

FIG.6

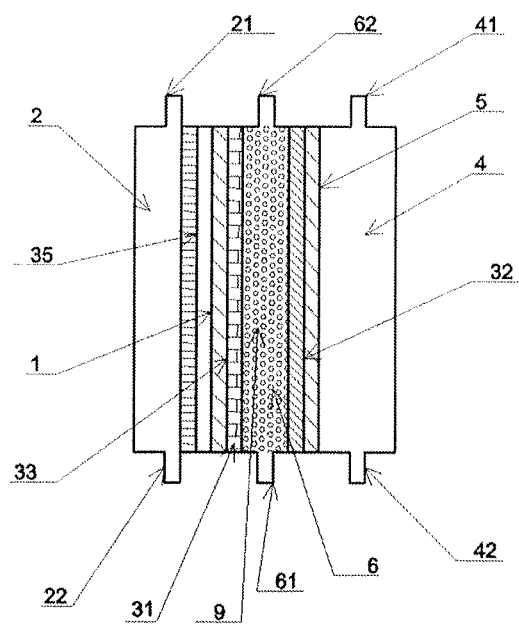

1   POROUS ANODE ELECTRODE
2   ANODE CHAMBER
21  ANODE CHAMBER OUTLET
22  ANODE CHAMBER INLET
31  PARTITIONING MEMBRANE 1
32  PARTITIONING MEMBRANE 2
33  FLUORINE-CONTAINING CATION
    EXCHANGE MEMBRANE
36  NON-WOVEN FABRIC
4   CATHODE CHAMBER
41  CATHODE CHAMBER OUTLET
42  CATHODE CHAMBER INLET
5   POROUS CATHODE ELECTRODE
6   INTERMEDIATE CHAMBER
61  INTERMEDIATE CHAMBER INLET
62  INTERMEDIATE CHAMBER OUTLET
9   ANION EXCHANGE RESIN

1   POROUS ANODE ELECTRODE
2   ANODE CHAMBER
31  PARTITIONING MEMBRANE 1
32  PARTITIONING MEMBRANE 2
33  FLUORINE-CONTAINING CATION
    EXCHANGE MEMBRANE
4   CATHODE CHAMBER
5   POROUS CATHODE ELECTRODE
6   INTERMEDIATE CHAMBER
9   ANION EXCHANGE RESIN
10  CATION RESIN TOWER
101 STIRRING PUMP
11  REGENERATED SALT ADDITION
    PORT
12  TAP WATER INLET

FIG.8

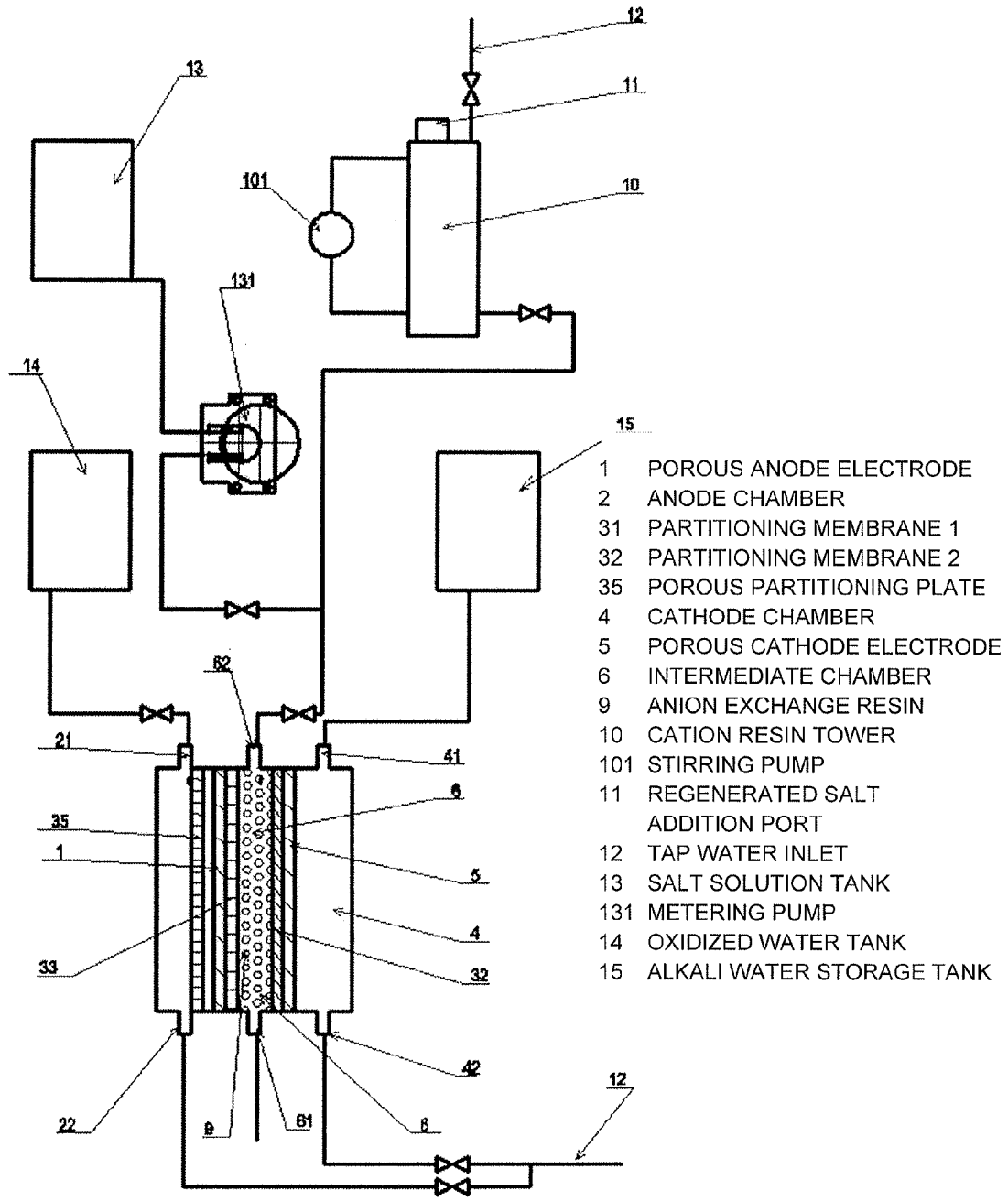

| | |
|---|---|
| 1 | POROUS ANODE ELECTRODE |
| 2 | ANODE CHAMBER |
| 31 | PARTITIONING MEMBRANE 1 |
| 32 | PARTITIONING MEMBRANE 2 |
| 35 | POROUS PARTITIONING PLATE |
| 4 | CATHODE CHAMBER |
| 5 | POROUS CATHODE ELECTRODE |
| 6 | INTERMEDIATE CHAMBER |
| 9 | ANION EXCHANGE RESIN |
| 10 | CATION RESIN TOWER |
| 101 | STIRRING PUMP |
| 11 | REGENERATED SALT ADDITION PORT |
| 12 | TAP WATER INLET |
| 13 | SALT SOLUTION TANK |
| 131 | METERING PUMP |
| 14 | OXIDIZED WATER TANK |
| 15 | ALKALI WATER STORAGE TANK |

METHOD FOR PRODUCING OXIDIZED WATER FOR STERILIZATION USE WITHOUT ADDING ELECTROLYTE

TECHNICAL FIELD

The present invention relates to a method for producing sterilization water that has a residual chlorine concentration suitable for sterilization and contains chlorine dioxide by electrolysis of tap water or the like basically without adding chlorine ions.

BACKGROUND ART

Conventionally, an electrolysis vessel for production of oxidized water for sterilization use is a two-chamber-type electrolysis vessel shown in FIG. 1 or a three-chamber-type electrolysis vessel shown in FIG. 2. In the two-chamber-type electrolysis vessel, a chlorine ion-dissolved water is supplied to an anode chamber by adding halogen salts such as salt to raw water. For example, when a salt solution is supplied, chlorine ions are oxidized to produce hypochlorite ions.

Specifically, in an oxidization reaction, chlorine ions are electrolytically oxidized to produce chlorine molecules. The chlorine molecules change in water into hypochlorite ions and hydrogen ions. Therefore, strongly acidic oxidized water is formed.

[Chemical Formula 1]

$$2Cl^- - 2e \Rightarrow Cl_2 \quad (1)$$

$$2HClO + 2H^+ \Leftrightarrow Cl_2 + 2H_2O \quad (2)$$

When the two-chamber-type electrolysis vessel is used, the ion concentration is insufficient. In order to promote the electrolytic oxidation reaction, it is necessary that the electrolysis voltage be enhanced or halogen salts such as salt be added to raw water. When halogen salts are added, highly acidic oxidized water is produced. Therefore, there is a problem of strong acidity in terms of maintenance and control of a device.

FIG. 2 shows the three-chamber-type electrolysis vessel in which an intermediate chamber is provided between an anode chamber and a cathode chamber. In a partitioning membrane, an ion exchange membrane is provided, and a porous electrode shown in FIG. 3 is used as an electrode. A salt solution or the like is supplied to the intermediate chamber. Chlorine ions in the intermediate chamber are transferred to the anode chamber. Part of the chlorine ions forms chlorine molecules in accordance with a chemical formula (1) to finally form hypochlorous acid that is strongly acidic. When an aqueous solution such as a salt solution is added to the intermediate chamber of the three-chamber-type electrolysis vessel and sterilization water containing residual chlorine is produced, there have been the following problems.

(i) The solution with which the intermediate chamber is filled is strongly acidic, i.e., as high as a pH of 1 or less, and the maintenance of the device is difficult.

(ii) Oxidized water that is strongly acidic with a pH of 2 to 3, and produces conventional oxidized water for sterilization use is produced.

(iii) When a general three-chamber-type electrolysis vessel is used, a main oxidizable substance is the hypochlorite ion. There have arisen problems in which the hypochlorite ion has defects in which the sterilization effect is lost by pH of alkalinity and the sterilization effect is decreased in the coexistence of organic substances.

The three-chamber-type electrolysis vessel provided with the intermediate chamber has had the problems described above. For example, when a salt solution is added to the intermediate chamber, chlorine ions are transferred to the anode chamber, and sodium ions are transferred to the cathode chamber. It is known that the pH in the intermediate chamber becomes acidic due to a difference in ionic permeability between partitioning membranes. By long-time electrolysis, the pH of liquid in the intermediate chamber may become strongly acidic to decrease the pH to 1 or less.

Such a strongly acidic liquid has corrosiveness, and adversely affects equipment.

As described above, oxidized water containing residual chlorine has conventionally been produced by electrolytic oxidation using a liquid of halogen salts such as a salt solution. In terms of maintenance and control of the device, there have arisen problems such as corrosion due to hydrochloric acid. In order to solve the problems such as corrosion, a first object was to produce sterilization water by electrolytically oxidizing natural water such as typical tap water without adding halogen acid.

It has been reported that hypochlorite ions exhibit sterilizing power and contribute to the residual chlorine concentration. The hypochlorite ions have the following disadvantages.

(1) The sterilizing power in a neutral pH range of 4 to 6 is maximum, the sterilizing power in an alkaline pH range of 8 or more is largely decreased, and the sterilizing power at a pH of 10 or more is substantially eliminated.

(2) When the hypochlorite ions coexist with bacteria and organic substances, the sterilizing power is known to be decreased.

A second object was to enhance the sterilizing power and maintain the sterilizing power in an alkaline range, and further to produce an oxidizable substance, which does not largely decrease the sterilizing power even in the coexistence of organic substances, by electrolysis.

An oxidizable chlorine compound that can be produced by electrolysis is chlorine dioxide in addition to hypochlorite ions. The following document has reported that the sterilizing power of chlorine dioxide is constant in a pH range of 6.0 to 10.0, and is stronger than that of hypochlorous acid. (Masahiko Takayama, et al., J. Antibact, Antifung, Agent VOL. 23, No. 7, pp. 401)

SUMMARY OF INVENTION

Technical Problem

An object to be achieved by the present invention is to provide an electrolysis method being capable of producing oxidized water for stabilization/disinfection use in a neutral pH range by anodically oxidizing raw water such as tap water effectively utilizing halogen ions such as chlorine ions contained in the raw water.

In order to produce oxidized water for sterilization use by an electrolysis operation, an aqueous solution for sterilization use has conventionally been produced by adding halogen ions, particularly chlorine ions from the outside, and oxidizing the chlorine ions to produce residual chlorine such as hypochlorous acid and chlorine dioxide. In this case, there has arisen a problem in which the pH exhibits strong acidity. The present invention aims to produce mild oxidized water for sterilization use by extremely decreasing the concentration of used halogen ions such as chlorine ions and preventing a decrease in pH.

In general, tap water contains chlorine ions or the like. In particular, when the chlorine ions or the like are efficiently used, oxidized water effective in sterilization is produced. In a case of tap water, the standard of tap water generally requires that the residual chlorine concentration caused by hypochlorous acid and the like is 0.1 ppm or more. In the present invention, oxidized water can be used to sterilize hands and feet, equipment, or the like. As the residual chlorine concentration is higher, the effect is enhanced. However, the concentration is restricted since tap water is used as a raw material. In the present invention, a target of the concentration is 0.5 ppm or more that is five times the standard of tap water, and preferably 1.0 ppm or more.

Solution to Problem

The present invention relates to a method for producing oxidized water for sterilization use which contains chlorine dioxide, the method including: electrolyzing tap water containing chlorine ions using a three-chamber-type electrolysis vessel in which an intermediate chamber is located between an anode chamber and a cathode chamber and is formed by providing partitioning membranes between the anode chamber and the cathode chamber;

trapping the chlorine ions dissolved in the tap water; and electrolytically oxidizing the trapped chlorine ions on the anode electrode;

wherein a partitioning membrane that isolates the anode chamber from the intermediate chamber has a fluorine-containing cation exchange membrane and an anion exchange membrane and a porous anode electrode is adhered onto the fluorine-containing cation exchange membrane in the partitioning membrane, wherein a partitioning membrane that isolates the cathode chamber from the intermediate chamber has a cation exchange membrane or an anion exchange membrane and a porous cathode electrode is adhered onto the partitioning membrane, and wherein the intermediate chamber is filled with an anion exchange resin.

Advantageous Effects of Invention

According to the present invention, oxidized water for sterilization/disinfection use in a neutral range can be produced.

BRIEF DESCRIPTION OF DRAWINGS

FIG. 1 is a schematic view illustrating a two-chamber-type electrolysis vessel.

FIG. 2 is a schematic view illustrating a three-chamber-type electrolysis vessel.

FIG. 5(a) is a schematic view illustrating a three-chamber-type electrolysis vessel used in Example 2.

FIG. 5(b) is a schematic view illustrating a three-chamber-type electrolysis vessel used in Example 2.

FIG. 6 is a schematic view illustrating a three-chamber-type electrolysis vessel used in Example 3.

FIG. 8 is a flow view in Example 6.

DESCRIPTION OF EMBODIMENTS

In tap water or the like, chlorine ions are dissolved at the maximum concentration of 200 ppm. When electrolysis is performed in a two-chamber-type electrolysis vessel shown in FIG. 1 or a simple three-chamber-type electrolysis vessel shown in FIG. 2 utilizing chlorine ions in such tap water, the residual chlorine concentration is 0.1 ppm or less, and is so low that the sterilization effect is not expected. When tap water is electrolyzed using the electrolysis vessel, the electric conductivity of tap water is insufficient to obtain target sterilization effect by electrolysis. Therefore, the electrolysis voltage is as high as 100 V or more at a current density of about 10 mA/cm2. Thus, a problem remains in practical terms. For practical use, it is preferred that a target chlorine concentration be achieved at an electrolysis voltage of about 30 V or less.

As described in Example 4, a method for decreasing the electrolysis voltage is a method of filling an intermediate chamber of the three-chamber-type electrolysis vessel in FIG. 2 with a cation exchange resin. The filled cation exchange resin makes it possible to decrease the electrolysis voltage at about 10 mA/cm2 to 20 V or less. However, the residual chlorine concentration is as low as about 0.1 ppm even in this case.

Figure 4:
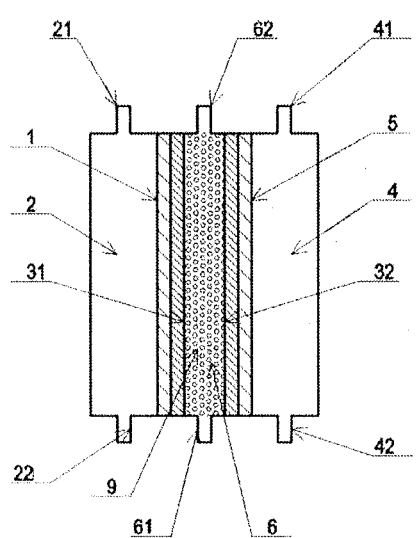
FIG. 4 is a schematic view illustrating a three-chamber-type electrolysis vessel used in Example 1.

In order to increase the residual chlorine concentration, the electrolysis vessel is improved as shown in FIGS. 4 to 6.

In FIG. 4, the intermediate chamber partitioned by an ion exchange membrane in FIG. 2 is filled with an anion exchange resin. As a partitioning membrane on an anode chamber side, an anion exchange membrane is used. When tap water is allowed to pass through the intermediate chamber, halogen ions such as chlorine ions are retained in the anion exchange resin and concentrated. When electrolysis is performed in this state, the residual chlorine concentration can be increased.

The anion exchange resin and a fluorine-containing cation exchange membrane used in the present invention will be described below. An amino group is bonded to the anion exchange resin as a functional group.

Such an anion exchange resin includes two kinds of exchange resins that are strong basic and weakly basic. In order to efficiently collect chlorine ions and the like in tap water, a strongly basic ion exchange resin is suitable. The strongly basic resin includes two kinds of I type that is bonded to a trimethylammonium group, and II type that is bonded to a dimethylethanolammonium group. The I type strongly basic resin is effective in terms of an efficiency of trapping chlorine ions and the like. Specifically, a strongly basic I-type anion exchange resin that is available from Mitsubishi Chemical Corporation is preferred.

On the other hand, in the fluorine-containing cation exchange membrane, a sulfate ion group is bonded to a fluorine resin as a functional group. Under an environment of fluorine resin, $H^+$ ions bonded to the sulfate ion groups are easily dissociated, and the $H^+$ ions can act as carriers during electrolysis. Therefore, it has been reported that pure water is also electrolyzable. As such a cation exchange membrane, Nafion 117 available from DuPont Co., and the like are useful. It has been reported that when an anode electrode is adhered onto the fluorine-containing cation exchange membrane and anode electrolysis is performed, ozone are generated (Proton exchange membrane fuel cell systems based on aromatic hydrocarbon and partially fluorinated disulfonated poly(Arlene ether)copolymers). Since the fluorine-containing cation exchange membrane is swelled in water, chlorine ions may pass through the membrane with high probability.

In order to increase the concentration of residual chlorine containing chlorine dioxide, the membrane permeability of chlorine ions may be important. In this case, when pores of 1 to 1,000 microns are given in the fluorine-containing cation exchange membrane, a reactivity of ozone with chlorine ions can be enhanced.

In FIG. 4, when the fluorine-containing cation exchange membrane is provided as the partitioning membrane on the anode chamber side between the anion exchange membrane and the anode electrode, the residual chlorine concentration can be further enhanced.

It has been known that when the anode electrode is specifically adhered onto the fluorine-containing cation exchange membrane and electrolysis is performed, the generation efficiency of ozone is increased. Produced ozone is subjected to an oxidation reaction with chlorine ions to produce high-order chlorine oxides, as shown by the following formula. (JPH08-134677, and JP2000-234191)

[Chemical Formula 2]

$$Cl^- + O_3 \rightarrow ClO_3^- \quad (3)$$

From the high-order chlorine oxides, chlorine dioxide is produced.

[Chemical Formula 3]

$$2ClO_3^- + O_2^- + 4H^+ \rightarrow 2ClO_2 + 3H_2O \quad (4)$$

$$ClO_3^- + OH. + 3H^+ \rightarrow ClO_2 + 2H_2O \quad (5)$$

$$2ClO_3^- + 2Cl^- + 4H^+ \rightarrow 2ClO_2 + 2H_2O + Cl_2 \quad (6)$$

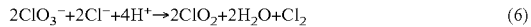

$Cl_2$, $ClO^-$, and $ClO_2$ have oxidative power, and an effect of sterilizing microorganisms. The substances contribute to the residual chlorine concentration, and exhibit sterilizing power.

Thus, when chlorine ions are directly added to residual chlorine generated by an electrolytic oxidation reaction, resulting in an oxidation reaction of the chlorine ions due to ozone, the residual chlorine concentration can be increased. Specifically, as shown in FIG. 6, the reaction efficiency of ozone produced at the anode electrode with chlorine ions is intended to be increased by locating a porous substance at the anode electrode on the anode chamber side in the anode chamber.

[Chemical Formula 4]

$$Cl + O_3 \rightarrow ClO_3^- \quad (7)$$

$$Cl_2 + 2H_2O \Leftrightarrow 2H^+ + 2Cl + O_2 \quad (8)$$

In order to efficiently perform an oxidation reaction of halogen ions, a planar permeable member is provided on an anode chamber side of a porous anode electrode. This configuration prevents direct contact of supplied water with the anode electrode, and increases the reaction efficiency of chlorine ions with ozone or the like. Furthermore, a reaction substance is supplied through pores of a non-woven fabric to a side of anode water.

Examples of the planar permeable member used in the present invention may include a porous partition plate, a porous film, and a non-woven fabric.

The porous partition plate or the porous film is a plate or a film that has many fine pores. The porous partition plate may constitute a porous partitioning membrane. In order to prevent a decrease in halogen ion concentration due to direct supply of raw water of the anode chamber to the anode electrode, in the planar permeable member, the porous partition plate is provided on the anode chamber side of the anode electrode. The porous partition plate or the porous film is desirably formed from a synthetic resin such as polypropylene and polyethylene as a material since the material is unlikely to cause deterioration such as rust due electrolytically oxidized water. As the plate or film that is formed from the resin, a plate or a film in which many pores with a diameter φ of 1 mm or less are formed is used. The pores may be mechanically formed, or a porous film having pores with a diameter φ of 100 μm or more may be used.

The non-woven fabric is a sheet-shaped fabric in which polymeric fibers are entangled without weaving. In general, fibers of polyethylene, polypropylene, polyethylene terephthalate, or the like are used. Since in the present invention, the non-woven fabric is combined with the anode electrode, resistance to oxidation is required. For this reason, a polytetrafluoroethylene (PTFE) resin non-woven fabric is suitable for the present invention. The pore size of the non-woven fabric is suitably 10 to 1,000 μm.

In order to promote the reaction of the oxidizable substance such as ozone produced on a surface of the anode electrode with unreacted chlorine ions or the like as described above, the anode chamber is divided by the planar permeable member.

In Table 1, the anode electrode side is called a mixing chamber. This planar permeable member prevents direct supply of raw water to the surface of the anode electrode and may improve the reaction efficiency of ozone with chlorine ions or the like.

The present invention aims to produce oxidized water for sterilization use by electrolytic oxidation of raw water which can be used for drinking such as tap water. However, the raw water generally includes dissolved divalent metal ions of alkaline earth metal such as calcium and magnesium. It has been known that the divalent metal ions are attached to a cathode electrode, and the cathode electrode is contaminated to increase the electrolysis voltage. Thus, an electrolysis operation is made difficult. In the present invention, when the concentration of the divalent metal ions in the raw water supplied to the intermediate chamber of the three-chamber-type electrolysis vessel is high, the raw water is allowed to pass through a cation exchange resin tower before supply of the raw water to the intermediate chamber to prevent contamination of the cathode electrode.

Example 1

As shown in FIG. 4, in a three-chamber electrolysis vessel that was provided with an intermediate chamber between an anode chamber 2 and a cathode chamber 4, a porous anode electrode 1 was adhered onto a partitioning membrane 1 (31) as an anion exchange membrane, and a porous cathode electrode was adhered onto a partitioning membrane 2 as a cation exchange membrane. An intermediate chamber 6 was provided between the partitioning membrane 1 and the partitioning membrane 2 (32), and was filled with an anion exchange resin 9. In the anion exchange resin 9, halogen ions such as chlorine ions, bromine ions, and iodine ions in tap water are trapped. As halogen ions contributing to electrolysis, the trapped halogen ions are used to perform oxidative decomposition. Use of the trapped ions improves an efficiency of producing $Cl_2$, $Br_2$, and $I_2$ which are sterilizable.

Example 2

In the anion exchange membrane of the partitioning membrane 1 (31) in the three-chamber-type electrolysis vessel of FIG. 4, it has been known that oxidation generally promotes deterioration. Therefore, a fluorine-containing cation exchange membrane 33 was interposed between the partitioning membrane 1 (31) including the anion exchange membrane and a porous anode electrode, as shown in FIG. 5(*a*). The presence of the fluorine-containing cation exchange membrane extends the life span of the anion exchange membrane. Further, it is important that the fluorine-containing cation exchange membrane is known to be swelled with water, also easily allow anions to pass, and have high generation efficiency of ozone. The generated ozone has sterilization property. By the ozone, chlorine ions are oxidized to produce chlorine dioxide ($Cl_2O$).

Furthermore, since the concentration of halogen ions such as chlorine ions is low, efficient use of the ions is required in the present invention. As shown in FIG. 5(*b*), a porous partitioning wall 35 is provided on a water communication side of the porous anode electrode to increase the concentration of halogen ions around the porous anode electrode in the three-chamber-type electrolysis vessel. In the present invention, a chamber separated by the anode electrode 1 and the porous partitioning membrane 35 is called a mixing chamber. When the porous partitioning membrane is provided, supply water to be supplied to anode water makes it possible to prevent a decrease in the concentration of halogen ions around the anode electrode. Thus, the electrolytic oxidation reaction efficiency is improved, and the residual chlorine concentration is improved.

Example 3

In order to improve the reactivity of ozone with chlorine ions in the three-chamber-type electrolysis vessels as shown in FIGS. 5(*a*) and 5(*b*), a surface of the anode electrode 1 was covered with a porous film in the three-chamber-type electrolysis vessel as shown in FIG. 6. Specifically, a fluorine-containing non-woven fabric 36 was used as the cover. The provision of the non-woven fabric makes it possible to increase the reaction efficiency of generated ozone gas with chlorine ions.

Example 4

Figure 3:
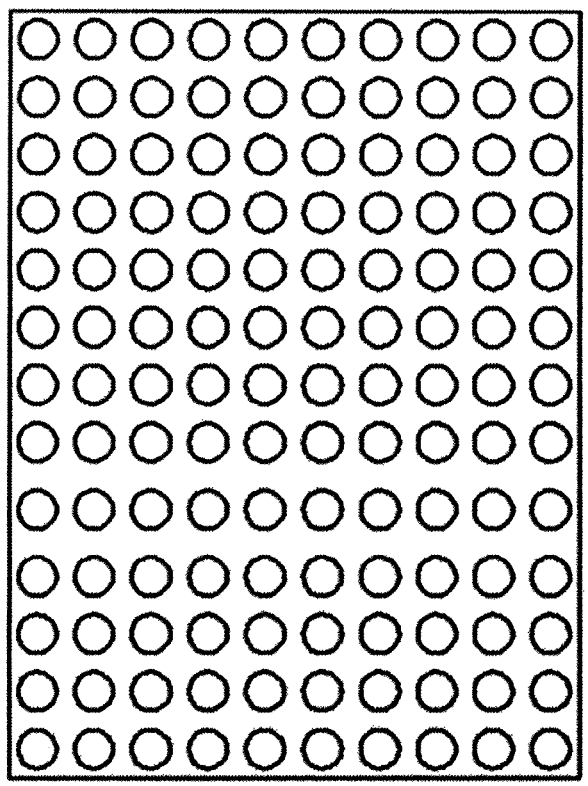
FIG. 3 is a plan view of a porous electrode.
Figure 7:
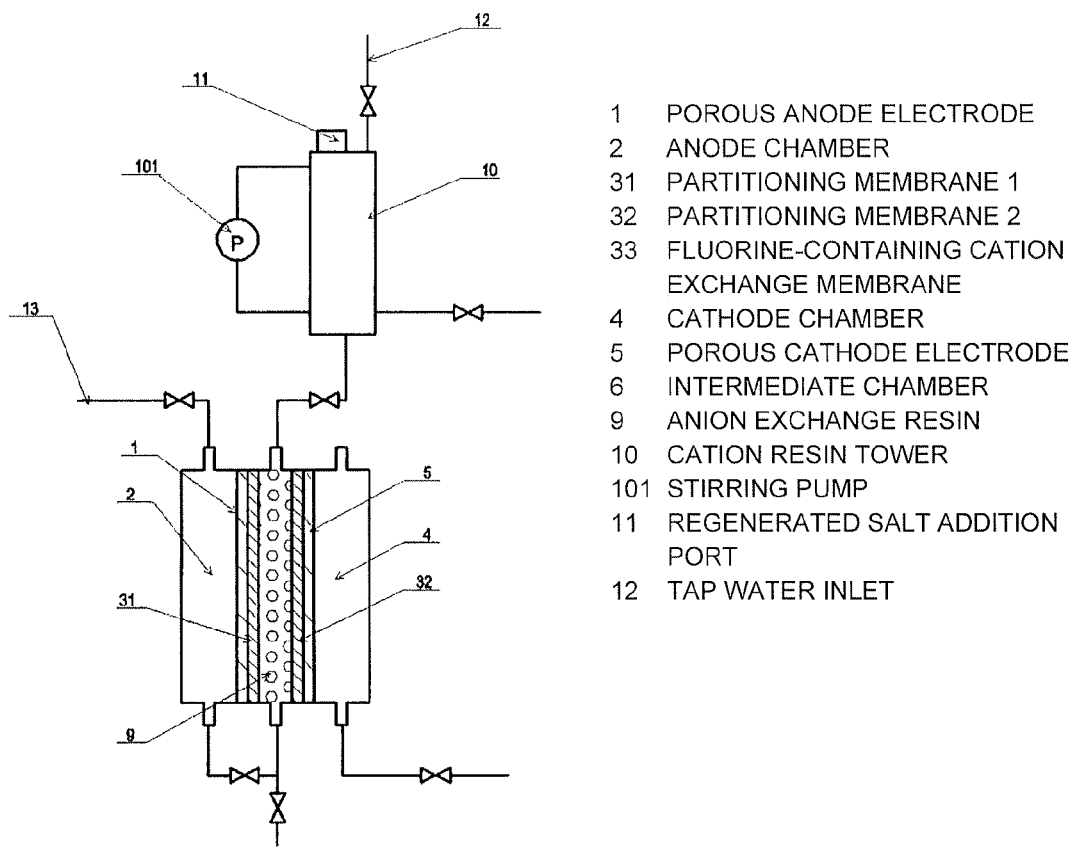
FIG. 7 is a flow view in Examples 4 and 5.

As shown in FIG. 3, platinum-plating titanium porous anode and cathode electrodes of 8×6 $cm^2$ were used, and the thickness of the intermediate chamber was 1 cm. The efficiencies of producing an oxidizable substance in the electrolysis vessels shown in FIGS. 2, 4, 5, and 6 were compared and investigated. A system shown in FIG. 7 was used as a test device. In the system of FIG. 7, tap water having a chlorine ion concentration of about 100 ppm is first allowed to pass through a cation exchange resin tower 10 to remove divalent metal ions that may considerably contaminate the cathode electrode. The divalent metal ion-filtered water was supplied to the intermediate chamber of each of the electrolysis vessels shown in FIGS. 2, 4, 5, and 6. A tap water inlet 12 is installed to inject tap water into the cation exchange resin tower 10. The ion exchange resin is efficiently regenerated by regularly adding a salt or the like as a regenerated salt from a regenerated salt addition port 11 and stirring an aqueous solution of regenerated salt using a stirring pump 101.

The electrolysis current was 8 A in each electrolysis vessel. The flow rate of tap water supplied to the anode chamber is 0.5 L/min, and the flow rate of tap water supplied to the intermediate chamber is 2.0 L/min.

When the simple three-chamber-type electrolysis vessel of FIG. 2 was used for comparison, the electrolysis voltage was increased and the electrolysis current was decreased to 1 A or less, and the residual chlorine concentration was 0.01 ppm or less. When the intermediate chamber of the three-chamber-type electrolysis vessel of FIG. 2 was filled with a cation exchange resin, the electrolysis voltage was decreased to 20 V or less, but the residual chlorine concentration was about 0.1 ppm. When the three-chamber-type electrolysis vessel in which the intermediate chamber was filled with an anion exchange resin as shown in FIG. 3 was used, the residual chlorine concentration became about 1.5 pm. From comparison of the values, an effect caused by charging the intermediate chamber with the anion exchange resin was revealed.

In order to enhance the durability of the anion exchange membrane of the partitioning membrane and effectively use ozone, a membrane in which the fluorine-containing cation exchange membrane and the anion exchange membrane were overlapped as shown in FIG. 5 so that the fluorine-containing cation exchange membrane was adhered onto the anode electrode was used as the partitioning membrane. When this electrolysis vessel was used, the residual chlorine concentration was about 2.0 ppm. In order to increase the transmittance of chlorine ions, 35 pores of about 0.5 microns were formed in this fluorine-containing cation exchange membrane.

When the electrolysis vessel in which the surface of the anode electrode was covered with the non-woven fabric as shown in FIG. 6 was used, the residual chlorine concentration in oxidized water produced became about 4.0 ppm. From these data, effectiveness of the present invention was exhibited.

TABLE 1

| STRUCTURE OF ELECTROLYSIS VESSEL | MIXING CHAMBER | PARTITIONING MEMBRANE | INTERMEDIATE CHAMBER | RESIDUAL CHLORINE CONCENTRATION (ppm) | RATIO OF CHLORINE DIOXIDE (%) | pH |
|---|---|---|---|---|---|---|
| THREE-CHAMBER-TYPE | FIG. 2 | — | — | ANION EXCHANGE MEMBRANE | ~0.1 | 0 | 6.1 |
| THREE-CHAMBER-TYPE | FIG. 2* | — | — | ANION EXCHANGE MEMBRANE | ~0.1 | 0 | 6.5 |

TABLE 1-continued

| STRUCTURE OF ELECTROLYSIS VESSEL | | MIXING CHAMBER | PARTITIONING MEMBRANE | | INTERMEDIATE CHAMBER | RESIDUAL CHLORINE CONCENTRATION (ppm) | RATIO OF CHLORINE DIOXIDE (%) | pH |
|---|---|---|---|---|---|---|---|---|
| THREE-CHAMBER-TYPE | FIG. 4 | — | — | ANION EXCHANGE MEMBRANE | ANION EXCHANGE RESIN | ~0.2 | 0 | 4.8 |
| THREE-CHAMBER-TYPE | FIG. 5 | — | FLUORINE-CONTAINING CATION EXCHANGE MEMBRANE | ANION EXCHANGE MEMBRANE | ANION EXCHANGE RESIN | ~2.0 | 25 | 4.5 |
| THREE-CHAMBER-TYPE | FIG. 6 | NON-WOVEN FABRIC | FLUORINE-CONTAINING CATION EXCHANGE MEMBRANE | ANION EXCHANGE MEMBRANE | ANION EXCHANGE RESIN | ~4.0 | 65 | 4.2 |

The mark "*"represents that an intermediate chamber of a three-chamber-type electrolysis vessel shown in FIG. 2 is filled with a cation exchange resin.

Example 5

FIG. 8 shows an example of a system capable of appropriately exchanging and supplying both of purified tap water and a salt solution to an intermediate chamber of a three-chamber-type electrolysis vessel. In this example, the electrolysis vessel shown in FIG. 5(b) was built in. In this electrolysis vessel, a partitioning membrane structure having the anion exchange membrane 31 and the fluorine-containing cation exchange membrane 33 is used, and the partitioning membrane of this structure is adhered onto the anode electrode 1. A porous partitioning membrane 35 is provided on a side of the anode chamber 2 that is an opposite side of the partitioning membrane structure. For the intermediate chamber of the electrolysis vessel, a method of supplying tap water having passed through the ion exchange resin tower 10 and a method of supplying a salt solution from a salt solution tank 13 using a metering pump 150 to the intermediate chamber can be selected.

In the system of FIG. 8, the salt solution tank was filled with a 15% salt solution, and the salt solution was supplied to the intermediate chamber at about 3 mL/min. The dimension of an electrode built in the electrolysis vessel was 6×8 cm$^2$, and the electrolysis current was 10 A. The flow rate of tap water supplied was 1 L/min. The residual chlorine concentration of electrolytically oxidized water produced was measured to be about 45 ppm. The ratio of chlorine dioxide in the oxidized water was 72%. In the measurement of chlorine dioxide, colorimetry using glycine and diethyl-p-phenylene diamine (DPD) was used.

Example 6

Figure 9:
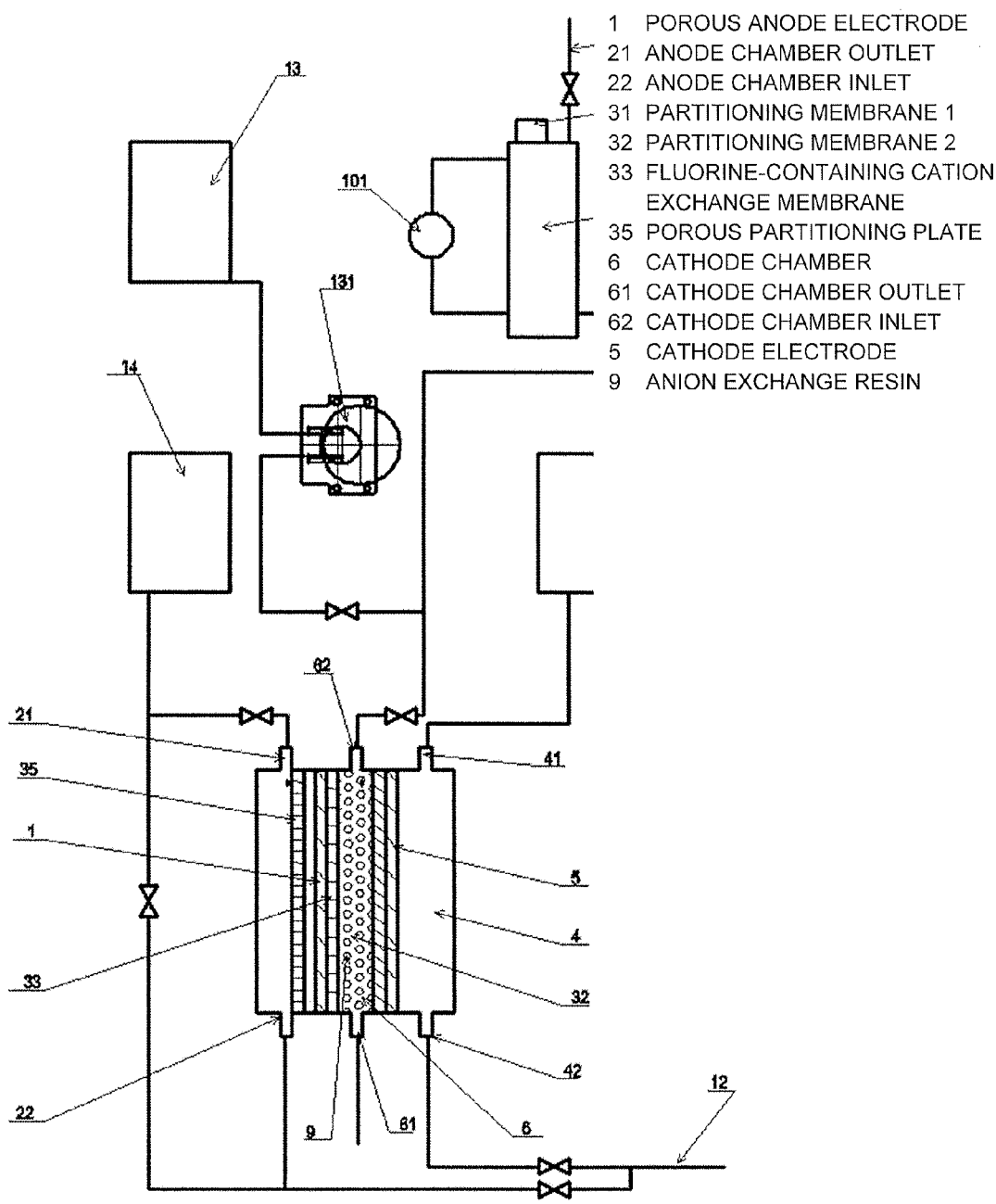
FIG. 9 is a flow view according to another embodiment of Example 6.

A system that is basically the same as the system of FIG. 8 and is provided with a bypass line that circumvents the anode chamber of the electrolysis vessel is shown in FIG. 9. When this system is used, the flow rate of tap water as raw water in the anode chamber can be largely decreased while the whole flow rate of oxidized water is maintained. When the flow rate in the anode chamber was restricted to 0.2 L/min and the whole flow rate of tap water was 1 L/min under the same electrolysis condition as in Example 5, the residual chlorine concentration was increased to 85 ppm.

Example 7

Figure 10:
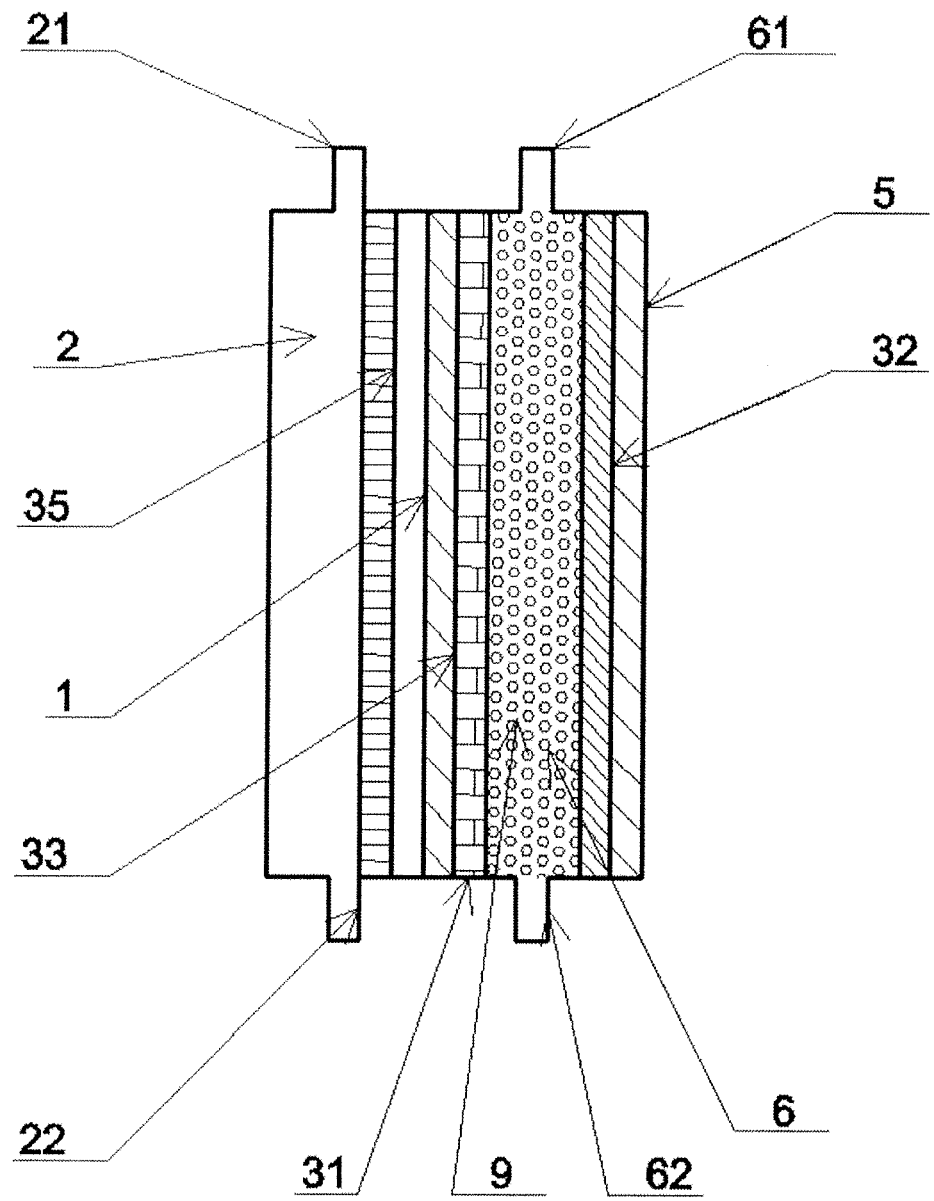
FIG. 10 is a schematic view illustrating a three-chamber-type electrolysis vessel used in Example 7.

Herein, a structure in which the three-chamber-type electrolysis vessel is improved so as to decrease the use amount of water is shown in FIG. 10. As shown in FIG. 10, a cathode chamber is removed, and an air electrode is used as a cathode electrode. When a fluorine-containing cation exchange membrane is used for a partitioning membrane on a cathode side, water in an intermediate chamber is partially transferred to a side of porous cathode electrode due to swelling property that is a property of the fluorine-containing cation exchange membrane. Therefore, electrolysis can be continually performed.

INDUSTRIAL APPLICABILITY

According to the present invention, oxidized water for sterilization/disinfection use in a neutral range can be produced. Therefore, the present invention is extremely useful for processing of foods or in a clinical setting.

REFERENCE SIGNS LIST 1 porous anode electrode
2 anode chamber
21 anode chamber outlet
22 anode chamber inlet
31 partitioning membrane 1
32 partitioning membrane 2
33 fluorine-containing cation exchange membrane
35 porous partitioning plate
36 non-woven fabric
4 cathode chamber
41 cathode chamber outlet
42 cathode chamber inlet
5 porous cathode electrode
6 intermediate chamber
61 intermediate chamber inlet
62 intermediate chamber outlet
9 anion exchange resin

The invention claimed is:

1. A method for producing oxidized water for sterilization use which contains chlorine dioxide, comprising:
   electrolyzing tap water containing chlorine ions using a three-chamber-type electrolysis vessel in which an intermediate chamber is located between an anode chamber and a cathode chamber and is formed by providing partitioning membranes between the anode chamber and the cathode chamber;
   trapping the chlorine ions dissolved in the tap water; and
   electrolytically oxidizing the trapped chlorine ions on the anode electrode;
   wherein a partitioning membrane that isolates the anode chamber from the intermediate chamber has a fluorine-containing cation exchange membrane and an anion exchange membrane and a porous anode electrode is adhered onto the fluorine-containing cation exchange membrane in the partitioning membrane, wherein a partitioning membrane that isolates the cathode chamber from the intermediate chamber has a cation exchange membrane or an anion exchange membrane and a porous cathode electrode is adhered onto the partitioning membrane, wherein the intermediate chamber is filled with an anion exchange resin, and wherein a planar permeable member is provided on an anode chamber side of the porous anode electrode to efficiently perform an oxidation reaction of chlorine ions into chlorine dioxide.

2. The method for producing oxidized water for sterilization use according to claim 1, wherein the electrolysis vessel that has a structure in which the fluorine-containing cation exchange membrane having pores with a diameter φ of 1 micron or more is adhered onto the porous anode electrode is used to increase the concentration of the chlorine dioxide.

3. The method for producing oxidized water for sterilization use according to claim 1, wherein a system provided with a bypass line parallel to a supplying line in the anode chamber of the three-chamber-type electrolysis vessel is utilized to increase the concentration of the chlorine dioxide.

4. The method for producing oxidized water for sterilization use according to claim 1, wherein raw water purified by a water-softening system filled with a cation exchange resin is utilized as water to be supplied to the intermediate chamber.

5. The method for producing oxidized water for sterilization use which contains chlorine dioxide according to claim 1, wherein the planar permeable member is a porous partitioning plate.

6. The method for producing oxidized water for sterilization use which contains chlorine dioxide according to claim 1, wherein the planar permeable member is a non-woven fabric.

7. The method for producing oxidized water for sterilization use according to claim 1, wherein a chlorine ion aqueous solution tank is provided, and a chlorine ion salt aqueous solution is supplied to the intermediate chamber by a metering pump, if necessary, resulting in electrolytic oxidation, to increase the concentration of the chlorine dioxide.

8. The method for producing oxidized water for sterilization use according to claim 1, wherein water obtained by causing raw water to pass through a cation exchange resin tower is supplied to the intermediate chamber to maintain the electrolysis efficiency for a long period of time, to thereby cause the water to contain chlorine dioxide.

* * * * *